United States Patent
Kim et al.

(10) Patent No.: US 10,434,463 B2
(45) Date of Patent: Oct. 8, 2019

(54) SEPARATION MEMBRANE FOR OLEFIN SEPARATION AND OLEFIN SEPARATION METHOD USING THE SAME

(71) Applicant: Korea Research Institute of Chemical Technology, Daejeon (KR)

(72) Inventors: Jeong Hoon Kim, Daejeon (KR); Su Young Moon, Gyeonggi-do (KR); Bong Jun Chang, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 16 days.

(21) Appl. No.: 15/920,962

(22) Filed: Mar. 14, 2018

(65) Prior Publication Data

US 2018/0272274 A1  Sep. 27, 2018

(30) Foreign Application Priority Data

Mar. 23, 2017  (KR) ........................ 10-2017-0037187

(51) Int. Cl.
| | |
|---|---|
| *B01D 69/02* | (2006.01) |
| *B01D 53/22* | (2006.01) |
| *B01D 69/12* | (2006.01) |
| *B01D 67/00* | (2006.01) |
| *C07C 7/144* | (2006.01) |
| *B01D 69/14* | (2006.01) |
| *B01D 71/02* | (2006.01) |
| *B01D 71/68* | (2006.01) |
| *B01D 71/12* | (2006.01) |
| *B01D 71/60* | (2006.01) |

(52) U.S. Cl.
CPC ....... *B01D 53/228* (2013.01); *B01D 67/0079* (2013.01); *B01D 69/02* (2013.01); *B01D 69/12* (2013.01); *B01D 69/148* (2013.01); *C07C 7/144* (2013.01); *B01D 67/0088* (2013.01); *B01D 71/022* (2013.01); *B01D 71/12* (2013.01); *B01D 71/60* (2013.01); *B01D 71/68* (2013.01); *B01D 2256/24* (2013.01); *B01D 2257/7022* (2013.01); *B01D 2323/30* (2013.01); *B01D 2325/14* (2013.01); *B01D 2325/16* (2013.01)

(58) Field of Classification Search
None
See application file for complete search history.

(56) References Cited

U.S. PATENT DOCUMENTS

| | | | | |
|---|---|---|---|---|
| 2005/0032246 A1* | 2/2005 | Brennan | ............ | G01N 33/5432 436/518 |
| 2011/0045379 A1* | 2/2011 | Ryou | ................... | B01D 53/228 429/479 |

FOREIGN PATENT DOCUMENTS

KR  10-1255761  9/2012

OTHER PUBLICATIONS

Kim et al. "Facilitated Transport Membrane for Ethylene/Ethane and Propylene/Propane Separation" Clean Technology 2007 13(1):79-84.

Xin et al. "Enhanced Interfacial Interaction and CO2 Separation Performance of Mixed Matrix Membrane by Incorporating Polyethyleneimine-Decorated Metal-Organic Frameworks" ACS Applied Materials & Interfaces 2015 pp. 1-43.

* cited by examiner

*Primary Examiner* — Tam M Nguyen
(74) *Attorney, Agent, or Firm* — Licata & Tyrrell P.C.

(57) ABSTRACT

A separation membrane for olefin separation and olefin separation method using the same are provided.

12 Claims, 1 Drawing Sheet

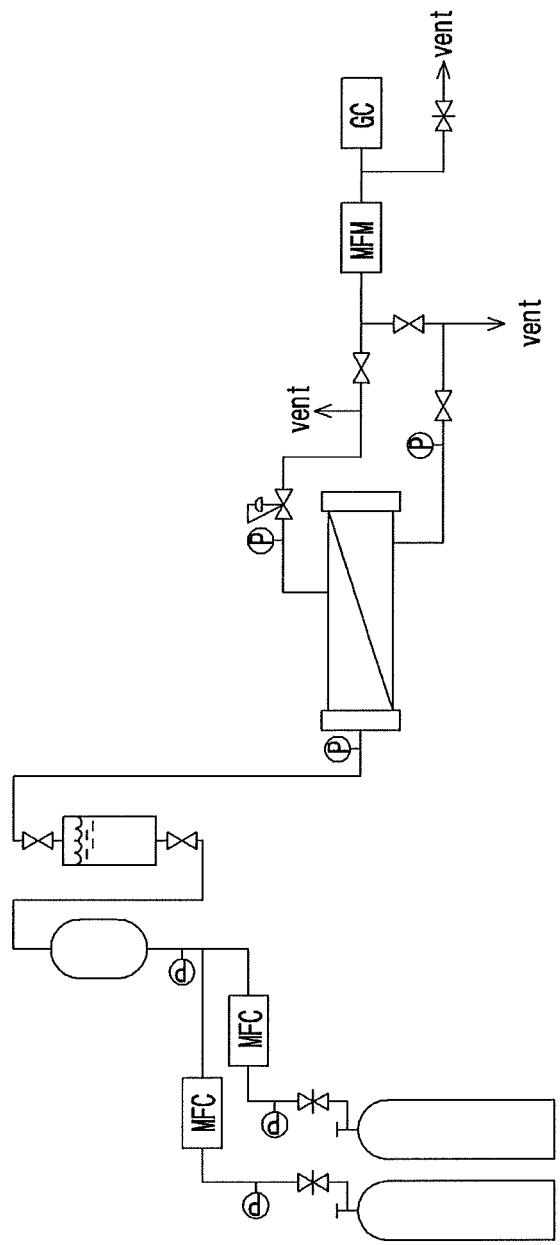

SEPARATION MEMBRANE FOR OLEFIN SEPARATION AND OLEFIN SEPARATION METHOD USING THE SAME

This patent application claims the benefit of priority from Korean Patent Application No. 10-2017-0037187 filed Mar. 23, 2017, the contents of which are herein incorporated by reference in their entirety.

BACKGROUND OF THE INVENTION

1. Field of the Invention

A separation membrane for olefin separation and olefin separation method using the same are provided.

2. Description of the Related Art

The production of the petrochemical product raw materials such as ethylene, propylene, and butene all over the world is growing more than 200 million tons annually and is continuously increasing.

Such ethylene, propylene and butene are generally produced by cracking of crude oil or dehydrogenation of hard paraffin. They are mainly present in the form of mixed gas of ethylene/ethane, propylene/propane, and butane/butene, indicating a high purity separation process is required to obtain each of those materials. A low temperature distillation process is generally used for separating those materials. However, as shown in the following table I, the difference of boiling points between the two materials, olefin and paraffin, is very small, in addition to the similarity of the sizes between them, and therefore simple separation is difficult and energy and plant costs consumed in the course of the low temperature distillation process are high.

TABLE I

|  | eth-ane | ethyl-ene | pro-pane | propyl-ene | n-butane | 1-butylene |
|---|---|---|---|---|---|---|
| Boiling Point(° C.) | −88.6 | −103.7 | −42.1 | −47.7 | −0.6 | −5 |
| $\sigma_{LJ}(A)$ * | 4.4 | 4.1 | 5.2 | 4.7 | 5.9 | 5.2 |

* Lennard-John's diameter of gas molecules

In particular, the energy used in the separation process of olefin/paraffin takes 0.3% of the total energy consumption in the world. So, if the distillation process can be simplified to 1/10, it is an important technology that can reduce manufacturing cost and greatly reduce global warming. Therefore, many new adsorption, absorption and membrane separation technologies have been studied to replace the distillation process.

Separation membrane technology is known to be appropriate for the separation of olefins because of low plant and operating energy costs. In particular, a facilitated transport membrane is used for separating olefins by impregnating water swelling polymers, ionic polymers, and polar organic compounds that can dissociate various transition metal ions (salts of Ag(I), Pd(II), Cu(I), and Pt(I)): for example, silver nitrate, copper chloride, and platinum sulfate, etc.) or transition metal nanoparticles capable of promoting transport by forming complexes with double bonds of olefins. Especially, the facilitated transport membrane using water swelling polymers or ionic polymers has been studied a lot due to the excellence in olefin separation performance. However, it still has limits and disadvantages of low permeability of the composite membrane resulted from the weak mechanical strength and poor durability in addition to the limited transition metal concentration (Korean Patent No. 10-1255761).

In a preferred embodiment of the present invention, the present invention provides a separation membrane for olefin separation, and a method for separating ethylene/ethane, propylene/propane, and butane/butene in room temperature and low pressure condition using the same.

SUMMARY OF THE INVENTION

It is an object of the present invention to provide a separation membrane for olefin separation comprising: aminated polymer, sulfonated polymer or mixtures thereof; and transition metal.

It is another object of the present invention to provide a method for separating olefin from the mixed gas of olefin and paraffin by using the separation membrane for olefin separation.

It is another object of the present invention to provide a composite membrane for olefin separation comprising: aminated polymer, sulfonated polymer or mixtures thereof; transition metal; and porous support.

It is another object of the present invention to provide a method for separating olefin from the mixed gas of olefin and paraffin by using the composite membrane for olefin separation.

To achieve the above objects, the present invention provides a separation membrane for olefin separation comprising: aminated polymer, sulfonated polymer or mixtures thereof; and transition metal.

The present invention also provides a method for separating olefin from the mixed gas of olefin and paraffin by using the separation membrane for olefin separation.

The present invention also provides a composite membrane for olefin separation comprising: aminated polymer, sulfonated polymer or mixtures thereof; transition metal; and porous support.

The present invention also provides a method for separating olefin from the mixed gas of olefin and paraffin by using the composite membrane for olefin separation.

Advantageous Effect

The separation/composite membrane for olefin separation according to the present invention is prepared by combining the conventional olefin separation membrane composed of aminated polymers with the polymers having sulfonic acid group capable of maintaining ionic bonding, such as transition metal ions, in a specific weight % range. Therefore, the separation/composite membrane for olefin separation displays a higher transition metal loading than the conventional separation membrane containing aminated polymers alone or sulfonated polymers alone, has a remarkably excellent at high pressure, displays a stable olefin permeability and olefin/paraffin selectivity, and has excellent mechanical properties due to cross-linking of poly ion complex membrane, suggesting that the separation/composite membrane for olefin separation of the present invention has a significantly improved durability and transition metal ion loading.

BRIEF DESCRIPTION OF THE DRAWINGS

FIG. 1 is a Schematic Diagram of Permeation Equipment.

DESCRIPTION OF THE PREFERRED EMBODIMENTS

Hereinafter, the present invention is described in detail.

The present invention provides a separation membrane for olefin separation comprising: aminated polymer, sulfonated polymer or mixtures thereof; and transition metal.

Due to the presence of the transition metal in the separation membrane, the separation membrane can exhibit selectivity for olefin. The aminated polymer forms a coordination bond with the transition metal, and the sulfonated polymer forms an ion bond with the transition metal. The transition metal may be in an ionic state. The transition metal may be crosslinked with aminated polymer and/or sulfonated polymer and/or mixtures thereof.

The sulfonated polymer concentration can be up to 80% by the weight of the separation membrane for olefin separation, or 30~70 weight %, 40~60 weight %, and more preferably 50 weight %, but not always limited thereto.

The transition metal above is not limited but is preferably selected from the group consisting of Ag, Cu, Ti, Hf, Zr, V, Nb, Ta, Mo, W, Tc, Re, Co, Rh, Ir, Ni, Pd, Pt, Zn, and Sn. Considering economical efficiency, Ag or Cu can be preferably selected. The transition metal above can be in the form of ions or nanoparticles, and the size thereof is preferably 0.5~50 nm.

The aminated polymer above is not limited but is one or more compounds selected from the group consisting of linear polyethyleneimine (LPEI), branched polyethyleneimine (BPEI), polydopamine, poly(vinylamine), poly(allylamine), poly(l-lysine), chitosan, aminated methylcellulose, and aminated ethylcellulose.

Further, the sulfonated polymer above can be selected from the group consisting of sulfonated polysulfone, sulfonated polyetherether ketone, sulfonated polyimide, sulfonated polyamide, sulfonated polycarbonate, sulfonated cellulose acetate, sulfonated polyethylene, sulfonated polypropylene, sulfonated polyvinylidene fluoride, sulfonated polyvinyl chloride, sulfonated polyester, sulfonated polyacrylonitrile, sulfonated polystyrene, sulfonated butadiene, and copolymers thereof. In a preferred embodiment of the present invention, the sulfonated polymer can be the sulfonated polysulfone of polysulfone represented by the following formula.

[Formula of polysulfone]

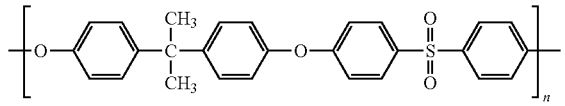

The n herein is an integer of 1~10,000.

The separation membrane further comprising electron acceptors.

The electron acceptors are one or more selected from the group consisting of Tetrathiafulvalene, p-benzoquinone, and 7,7,8,8-tetracyanoquinodimethane (TCNQ).

Strong electron acceptors can induce a positive charge on a transition metal ion or nano metal surface. These electron acceptors can enhance long-term stability of membranes by maintaining metal ion or positive charge of nano metal surface.

The electron acceptors is contained in an amount of 1~15 parts by weight based on 100 parts by weight of the separation membrane.

The present invention provides, in a preferred embodiment of the invention, a method for separating olefin from the mixed gas of olefin and paraffin by using the separation membrane for olefin separation.

Herein, the "using" includes contacting the separation membrane for olefin separation comprising transition metal and aminated polymer with the mixed gas of olefin and paraffin and inducing selective permeation of only one gas included in the mixed gas through the separation membrane, but not always limited thereto.

The "separation" herein includes a method to concentrate one gas of the mixed gas alone at a high concentration by selectively separating the one from the mixed gas of olefin and paraffin by making it pass through the separation membrane, but not always limited thereto. The one gas can be, for example, olefin.

The temperature and the pressure for the contact of the mixed gas with the separation membrane for olefin separation are not limited, but can be exemplified by the temperature of −20°~90°, −10°~80°, 0°~70°, 5°~60°, 10°~50°, 15°~40°, 18°~30°, preferably by the temperature of 20°~25°, and more preferably by room temperature (about 23°).

The pressure can be set in the range between 1~50 bar, 2~45 bar, 3~40 bar, 4~35 bar, 5~30 bar, 5~25 bar, 5~20 bar, preferably 5~15 bar, and more preferably 8~12 bar.

The present invention also provides a composite membrane for olefin separation comprising: aminated polymer, sulfonated polymer or mixtures thereof; transition metal; and porous support.

The present invention also provides a method for separating olefin from the mixed gas of olefin and paraffin by using the composite membrane for olefin separation.

At this time, since the aminated polymer, sulfonated polymer, and transition metal are the same as those described above, a detailed description thereof will be omitted in order to avoid redundant explanations.

The porous support can be selected from the group consisting of the porous supports, metal porous supports, and ceramic porous supports made of polysulfone, polyvinylidene fluoride, polyamide imide, polyether imide, or polyester, but not always limited thereto.

The present inventors performed experiments to evaluate the separation performance of the composite membrane for olefin separation of the present invention. As a result, when the composite membrane for olefin separation of the present invention included sulfonated polysulfone or sulfonated polyetherether ketone (PEEK) at the concentration of 30~70 weight % by the total weight of the polymer ion complex membrane composed of transition metal, polyethyleneimine or chitosan, and sulfonated polysulfone or polyetherether ketone (PEEK), etc, the permeability and selectivity to olefin were remarkably excellent. The olefin/paraffin separation process was performed for 30 days and the separation performance of the membrane was confirmed to be maintained as excellent consistently (see Experimental Examples 1 and 2).

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Composite Membrane for Olefin Separation 1

1.6 wt % sulfonated polysulfone solution (sulfonated polysulfone (Udel 6100): 1.5 g, water: 95.5 mL, acetic acid: 2.9 mL) was prepared, which was stirred for 12 hours. Chitosan (Sigma-Aldrich) was added thereto at the concentration of 0~100 weight % by the total weight of the finally prepared separation membrane. The mixture was stirred again, followed by filtering to eliminate impurities. At this time, the finally prepared separation membrane indicates the separation membrane containing sulfonated polysulfone, chitosan, and transition metal which would be explained hereinafter.

The mixed solution excluding impurities above was casted on a polysulfone support, the porous support, leading to the formation of a regular membrane at room temperature. 5 hours later, the composite membrane (separation membrane+polysulfone, the porous support) was neutralized by impregnation in 500 mL of 1 M NaOH aqueous solution for 12 hours, and then washed with a large amount of water to remove NaOH.

To impregnate the composite membrane washed with water with silver nitrate, the composite membrane was soaked in 3 M silver nitrate (AgNO$_3$) aqueous solution for 12 hours, which was later used as a separation membrane without further washing.

As a control, a composite membrane was prepared without adding chitosan or sulfonated polysulfone, and the performance of the composite membrane was evaluated.

Example 2: Preparation of Composite Membrane for Olefin Separation 2

A composite membrane for olefin separation was prepared in the same manner as described in <Example 1> except that 5 M copper chloride aqueous solution was used instead of 3 M silver nitrate (AgNO3) aqueous solution, polyethyleneimine (Sigma-Aldrich) was used instead of chitosan, and sulfonated polyetherether ketone (BASF, PEEK) was used instead of sulfonated polysulfone.

As a control, a composite membrane was prepared without adding polyethyleneimine or sulfonated polyetherether ketone, and the performance of the composite membrane was evaluated.

Experimental Example 1: Evaluation of Separation Performance of Composite Membrane for Olefin Separation 1

To evaluate the separation performance of the composite membrane for olefin separation prepared in the present invention, permeation equipment was equipped as shown in FIG. 1.

In the schematic diagram of permeation equipment of FIG. 1, the two bombes in the right bottom supply olefin gas and paraffin gas independently, and the humidifier connected to the two bombes is a device to supply humidity to the mixed gas of olefin and paraffin. The Membrane test cell connected to the humidifier is equipped with the composite membrane for olefin separation prepared in Examples 1 and 2, which is to measure the olefin permeability and selectivity. At this time, the permeability is expressed in units of GPU by calculating the permeation amount of the separation membrane from the area of the separation membrane, the permeation time, and the permeation pressure. The selectivity is calculated by the ratio of the permeability of pure gas of olefin to paraffin. To evaluate the permeation performance, the composite membrane for olefin separation of the present invention was prepared in the size of 100 cm$^2$ and the pressure was adjusted in the range between 5 and 15 bar.

<1-1> Ethylene/Ethane

Ethylene/ethane gas was provided through the bombe. The permeability and selectivity were calculated in the membrane test cell equipped with the composite membrane prepared in Example 1. The results are shown in Tables 1 and 2 below.

TABLE 1

| Sulfonated polysulfone content of separation membrane (wt %) | Ethylene permeability (GPU) | | |
|---|---|---|---|
| | 5 bar | 10 bar | 15 bar |
| 0 | 24.1 | 13.9 | 8.3 |
| 30 | 33.8 | 23.8 | 18.1 |
| 50 | 32.6 | 25.6 | 20.1 |
| 70 | 26.1 | 24.1 | 19.1 |
| 100 | 20.9 | 8.2 | 7.9 |

TABLE 2

| Sulfonated polysulfone content of separation membrane (wt %) | Ethylene/ethane selectivity ($\alpha$) | | |
|---|---|---|---|
| | 5 bar | 10 bar | 15 bar |
| 0 | 170 | 140 | 121 |
| 30 | 210 | 185 | 160 |
| 50 | 260 | 220 | 200 |
| 70 | 220 | 200 | 190 |
| 100 | 150 | 135 | 110 |

As shown in Table 1 and Table 2 above, the composite membrane composed of the separation membrane containing sulfonated polysulfone at the concentration of 30~70 weight % displayed remarkably excellent permeability and selectivity, compared with the composite membrane comprising the separation membrane containing sulfonated polysulfone alone or chitosan alone.

In addition, the composite membrane comprising the separation membrane containing sulfonated polysulfone at the concentration of 30~70 weight % displayed the improvement of separation performance even when the pressure was increased from 5 bar to 15 bar, compared with the composite membrane comprising the separation membrane containing sulfonated polysulfone alone or chitosan alone. The olefin/paraffin separation experiment was performed for 30 days. As a result, it was confirmed that the separation performance was maintained as excellent.

This was resulted from the improvement of durability by maintaining the polymer structure stably and firmly through the ionic cross-linking between the two polymers, sulfonated polysulfone and chitosan.

<1-2> Propylene/Propane

The following experiment was performed by the same manner as described in Example <1-1> except that propylene/propane gas was used as the mixed gas and the results are shown in Tables 3 and 4 below.

TABLE 3

| Sulfonated polysulfone content of separation membrane (wt %) | Propylene permeability (GPU) | | |
|---|---|---|---|
| | 5 bar | 10 bar | 15 bar |
| 10 | 14.1 | 10.9 | 8.3 |
| 30 | 23.8 | 18.8 | 16.1 |
| 50 | 22.6 | 19.6 | 18.1 |
| 70 | 21.1 | 18.1 | 16.1 |
| 90 | 14.9 | 10.2 | 7.9 |

TABLE 4

| Sulfonated polysulfone content of separation membrane (wt %) | propylene/propane selectivity ($\alpha$) | | |
|---|---|---|---|
| | 5 bar | 10 bar | 15 bar |
| 10 | 150 | 136 | 121 |
| 30 | 180 | 165 | 140 |
| 50 | 198 | 170 | 155 |
| 70 | 170 | 157 | 140 |
| 90 | 148 | 121 | 105 |

As shown in Table 3 and Table 4 above, the composite membrane composed of the separation membrane containing sulfonated polysulfone at the concentration of 30~70 weight % displayed remarkably excellent permeability and selectivity, compared with the composite membrane comprising the separation membrane containing sulfonated polysulfone alone or chitosan alone.

In addition, the composite membrane comprising the separation membrane containing sulfonated polysulfone at the concentration of 30~70 weight % displayed the improvement of separation performance even when the pressure was increased from 5 bar to 15 bar, compared with the composite membrane comprising the separation membrane containing sulfonated polysulfone alone or chitosan alone. The olefin/paraffin separation experiment was performed for 30 days. As a result, it was confirmed that the separation performance was maintained as excellent.

This was resulted from the improvement of durability by maintaining the polymer structure stably and firmly through the ionic cross-linking between the two polymers, sulfonated polysulfone and chitosan.

<1-3> Butene/Butane

The following experiment was performed by the same manner as described in Example <1-1> except that butene/butane gas was used as the mixed gas and the results are shown in Tables 5 and 6 below.

TABLE 5

| Sulfonated polysulfone content of separation membrane (wt %) | Butene permeability (GPU) | | |
|---|---|---|---|
| | 5 bar | 10 bar | 15 bar |
| 0 | 10.1 | 7.9 | 4.3 |
| 30 | 13.8 | 12.8 | 10.1 |
| 50 | 15.6 | 13.6 | 11.1 |
| 70 | 13.1 | 11.1 | 10.1 |
| 100 | 9.9 | 6.2 | 5.9 |

TABLE 6

| Sulfonated polysulfone content of separation membrane (wt %) | Butene/butane selectivity ($\alpha$) | | |
|---|---|---|---|
| | 5 bar | 10 bar | 15 bar |
| 0 | 130 | 116 | 91 |
| 30 | 160 | 145 | 120 |
| 50 | 178 | 150 | 145 |
| 70 | 170 | 137 | 120 |
| 100 | 138 | 116 | 95 |

As shown in Table 5 and Table 6 above, the composite membrane composed of the separation membrane containing sulfonated polysulfone at the concentration of 30~70 weight % displayed remarkably excellent permeability and selectivity, compared with the composite membrane comprising the separation membrane containing sulfonated polysulfone alone or chitosan alone.

In addition, the composite membrane comprising the separation membrane containing sulfonated polysulfone at the concentration of 30~70 weight % displayed the improvement of separation performance even when the pressure was increased from 5 bar to 15 bar, compared with the composite membrane comprising the separation membrane containing sulfonated polysulfone alone or chitosan alone. The olefin/paraffin separation experiment was performed for 30 days. As a result, it was confirmed that the separation performance was maintained as excellent.

This was resulted from the improvement of durability by maintaining the polymer structure stably and firmly through the ionic cross-linking between the two polymers, sulfonated polysulfone and chitosan.

Experimental Example 2: Evaluation of Separation Performance of Composite Membrane for Olefin Separation 2

The separation performance of the composite membrane for olefin separation was evaluated by the same manner as described in Experimental Example 1 by using the polyethyleneimine/sulfonated polyetherether ketone (polyether ether ketone, PEEK) polymer ion complex composite membrane prepared in Example 2 instead of using the composite membrane prepared in Example 1.

<2-1> Ethylene/Ethane

Ethylene/ethane gas was provided through the bombe. The permeability and selectivity were calculated in the membrane test cell equipped with the composite membrane prepared in Example 2. The results are shown in Tables 7 and 8 below.

TABLE 7

| Sulfonated polyetherether ketone content of separation membrane (wt %) | Ethylene permeability (GPU) | | |
|---|---|---|---|
| | 5 bar | 10 bar | 15 bar |
| 0 | 28.1 | 17.9 | 12.3 |
| 30 | 37.8 | 27.8 | 22.1 |
| 50 | 37.6 | 35.6 | 28.1 |
| 70 | 32.1 | 29.1 | 23.1 |
| 100 | 25.9 | 18.2 | 13.9 |

TABLE 8

| Sulfonated polyetherether ketone content of separation | Ethylene/ethane selectivity ($\alpha$) | | |
|---|---|---|---|
| membrane (wt %) | 5 bar | 10 bar | 15 bar |
| 0 | 150 | 120 | 101 |
| 30 | 190 | 165 | 140 |
| 50 | 240 | 200 | 180 |
| 70 | 200 | 170 | 160 |
| 100 | 150 | 110 | 90 |

As shown in Table 7 and Table 8 above, the composite membrane composed of the separation membrane containing sulfonated polyetherether ketone at the concentration of 30~70 weight % displayed remarkably excellent permeability and selectivity, compared with the composite membrane comprising the separation membrane containing polyethyleneimine alone or sulfonated polyetherether ketone alone.

In addition, the composite membrane comprising the separation membrane containing sulfonated polyetherether ketone at the concentration of 30~70 weight % displayed the improvement of separation performance even when the pressure was increased from 5 bar to 15 bar, compared with the composite membrane comprising the separation membrane containing polyethyleneimine alone or sulfonated polyetherether ketone alone. The olefin/paraffin separation experiment was performed for 30 days. As a result, it was confirmed that the separation performance was maintained as excellent.

This was resulted from the improvement of durability by maintaining the polymer structure stably and firmly through the ionic cross-linking between the two polymers, sulfonated polyetherether ketone and polyethylene imine.

<2-2> Propylene/Propane

The following experiment was performed by the same manner as described in Example <2-1> except that propylene/propane gas was used as the mixed gas and the results are shown in Tables 9 and 10 below.

TABLE 9

| Sulfonated polyetherether ketone content of separation | Propylene permeability (GPU) | | |
|---|---|---|---|
| membrane (wt %) | 5 bar | 10 bar | 15 bar |
| 10 | 17.1 | 14.9 | 12.3 |
| 30 | 27.8 | 22.8 | 20.1 |
| 50 | 28.6 | 26.6 | 24.1 |
| 70 | 25.1 | 23.1 | 21.1 |
| 90 | 16.9 | 11.2 | 8.9 |

TABLE 10

| Sulfonated polyetherether ketone content of separation | Propylene/propane selectivity ($\alpha$) | | |
|---|---|---|---|
| membrane (wt %) | 5 bar | 10 bar | 15 bar |
| 10 | 135 | 126 | 94 |
| 30 | 150 | 135 | 124 |
| 50 | 168 | 150 | 145 |
| 70 | 150 | 137 | 130 |
| 90 | 128 | 105 | 85 |

As shown in Table 9 and Table 10 above, the composite membrane composed of the separation membrane containing sulfonated polyetherether ketone at the concentration of 30~70 weight % displayed remarkably excellent permeability and selectivity, compared with the composite membrane comprising the separation membrane containing polyethyleneimine alone or sulfonated polyetherether ketone alone.

In addition, the composite membrane comprising the separation membrane containing sulfonated polyetherether ketone at the concentration of 30~70 weight % displayed the improvement of separation performance even when the pressure was increased from 5 bar to 15 bar, compared with the composite membrane comprising the separation membrane containing polyethyleneimine alone or sulfonated polyetherether ketone alone. The olefin/paraffin separation experiment was performed for 30 days. As a result, it was confirmed that the separation performance was maintained as excellent.

This was resulted from the improvement of durability by maintaining the polymer structure stably and firmly through the ionic cross-linking between the two polymers, sulfonated polyetherether ketone and polyethylene imine.

<2-3> Butene/Butane

The following experiment was performed by the same manner as described in Example <2-1> except that butene/butane gas was used as the mixed gas and the results are shown in Tables 11 and 12 below.

TABLE 11

| Sulfonated polyetherether ketone content of separation | Butene permeability (GPU) | | |
|---|---|---|---|
| membrane (wt %) | 5 bar | 10 bar | 15 bar |
| 0 | 12.1 | 8.9 | 5.3 |
| 30 | 14.8 | 14.8 | 12.1 |
| 50 | 17.6 | 15.6 | 13.1 |
| 70 | 15.1 | 14.1 | 12.1 |
| 100 | 10.9 | 8.2 | 6.0 |

TABLE 12

| Sulfonated polyetherether ketone content of separation | Butene/butane selectivity ($\alpha$) | | |
|---|---|---|---|
| membrane (wt %) | 5 bar | 10 bar | 15 bar |
| 0 | 100 | 86 | 61 |
| 30 | 120 | 105 | 100 |
| 50 | 148 | 135 | 131 |
| 70 | 130 | 127 | 111 |
| 100 | 118 | 76 | 65 |

As shown in Table 11 and Table 12 above, the composite membrane composed of the separation membrane containing sulfonated polyetherether ketone at the concentration of 30~70 weight % displayed remarkably excellent permeability and selectivity, compared with the composite membrane comprising the separation membrane containing polyethyleneimine alone or sulfonated polyetherether ketone alone.

In addition, the composite membrane comprising the separation membrane containing sulfonated polyetherether ketone at the concentration of 30~70 weight % displayed the improvement of separation performance even when the pressure was increased from 5 bar to 15 bar, compared with the composite membrane comprising the separation membrane containing polyethyleneimine alone or sulfonated polyetherether ketone alone. The olefin/paraffin separation experiment was performed for 30 days. As a result, it was confirmed that the separation performance was maintained as excellent.

This was resulted from the improvement of durability by maintaining the polymer structure stably and firmly through the ionic cross-linking between the two polymers, sulfonated polyetherether ketone and polyethylene imine.

Example 3: Preparation of Separation Membrane for Olefin Separation 1

A separation membrane consisting of sulfonated polysulfone, chitosan, and transition metal was prepared in a similar manner to Example 1.

At this time, the separation membrane was prepared by controlling the sulfonated polysulfone to be contained in an amount of 50% by weight based on 100% by weight of the separation membrane.

Example 4: Preparation of Separation Membrane for Olefin Separation 2

A separation membrane was prepared in the same manner as Example 3 except that the separation membrane further comprising Tetrathiafulvalene as an electron acceptor.

The Tetrathiafulvalene is contained in the separation membrane in an amount of 7 parts by weight based on 100 parts by weight of the separation membrane composed of sulfonated polysulfone, chitosan and transition metal.

Example 5: Preparation of Separation Membrane for Olefin Separation 3

A separation membrane was prepared in the same manner as Example 3 except that the separation membrane further comprising p-benzoquinone as an electron acceptor.

The p-benzoquinone is contained in the separation membrane in an amount of 7 parts by weight based on 100 parts by weight of the separation membrane composed of sulfonated polysulfone, chitosan and transition metal.

Example 6: Preparation of Separation Membrane for Olefin Separation 4

A separation membrane was prepared in the same manner as Example 3 except that the separation membrane further comprising 7,7,8,8-tetracyanoquinodimethane (TCNQ) as an electron acceptor.

The 7,7,8,8-tetracyanoquinodimethane (TCNQ) is contained in the separation membrane in an amount of 7 parts by weight based on 100 parts by weight of the separation membrane composed of sulfonated polysulfone, chitosan and transition metal.

Experimental Example 3: Evaluation of Separation Performance of Separation Membrane for Olefin Separation 3

The separation performance of the separation membrane for olefin separation was evaluated by the same manner as described in Experimental Example 1 by using Example 3 to 6 instead of using the composite membrane prepared in Example 1. The results are shown in Tables 13 and 18 below.

<3-1> Ethylene/Ethane

TABLE 13

| Separation membrane | Ethylene permeability (GPU) | | |
|---|---|---|---|
| | 5 bar | 10 bar | 15 bar |
| Example 3 | 32.6 | 25.6 | 20.1 |
| Example 4 | 48.2 | 42.1 | 39.5 |
| Example 5 | 47.5 | 43.1 | 40.7 |
| Example 6 | 48.5 | 44.0 | 41.0 |

TABLE 14

| Separation membrane | Ethylene/ethane selectivity (α) | | |
|---|---|---|---|
| | 5 bar | 10 bar | 15 bar |
| Example 3 | 260 | 220 | 200 |
| Example 4 | 375 | 354 | 330 |
| Example 5 | 380 | 365 | 335 |
| Example 6 | 377 | 359 | 332 |

<3-2> Propylene/Propane

TABLE 15

| Separation membrane | Propylene permeability (GPU) | | |
|---|---|---|---|
| | 5 bar | 10 bar | 15 bar |
| Example 3 | 22.6 | 19.6 | 18.1 |
| Example 4 | 38.2 | 37.0 | 35.9 |
| Example 5 | 38.9 | 36.8 | 36.2 |
| Example 6 | 38.5 | 36.9 | 36.1 |

TABLE 16

| Separation membrane | Propylene/propane selectivity (α) | | |
|---|---|---|---|
| | 5 bar | 10 bar | 15 bar |
| Example 3 | 198 | 170 | 155 |
| Example 4 | 310 | 301 | 285 |
| Example 5 | 315 | 298 | 290 |
| Example 6 | 311 | 303 | 295 |

<3-3> Butene/Butane

TABLE 17

| Separation membrane | Butene permeability (GPU) | | |
|---|---|---|---|
| | 5 bar | 10 bar | 15 bar |
| Example 3 | 15.6 | 13.6 | 11.1 |
| Example 4 | 35.7 | 30.5 | 28.9 |
| Example 5 | 36.0 | 31.0 | 29.2 |
| Example 6 | 36.1 | 30.7 | 28.5 |

TABLE 18

| Separation membrane | Butene/butane selectivity (α) | | |
|---|---|---|---|
| | 5 bar | 10 bar | 15 bar |
| Example 3 | 178 | 150 | 145 |
| Example 4 | 301 | 295 | 264 |
| Example 5 | 305 | 297 | 269 |
| Example 6 | 310 | 291 | 270 |

As shown in Tables 13 to 18 above,

The separation membranes of Examples 4 to 6, which further contain an electron acceptor, exhibit a significantly better permeability and selectivity than the separation membrane of Example 3 which does not contain an electron acceptor.

What is claimed is:

1. A separation membrane for olefin separation comprising:
   aminated polymer, sulfonated polymer or mixtures thereof;
   transition metal; and
   electron acceptors.

2. The separation membrane for olefin separation according to claim 1,
   when the separation membrane for olefin separation comprise the mixtures of aminated polymer and sulfonated polymer,
   the sulfonated polymer is included in the separation membrane for olefin separation at the concentration of up to 80 weight %.

3. The separation membrane for olefin separation according to claim 1,
   when the separation membrane for olefin separation comprise the mixtures of aminated polymer and sulfonated polymer,
   the sulfonated polymer is included in the separation membrane for olefin separation at the concentration of 30~70 weight %.

4. The separation membrane for olefin separation according to claim 1,
   when the separation membrane for olefin separation comprise the mixtures of aminated polymer and sulfonated polymer,
   the sulfonated polymer is included in the separation membrane for olefin separation at the concentration of 50 weight %.

5. The separation membrane for olefin separation according to claim 1,
   wherein the aminated polymer is selected from the group consisting of chitosan, linear polyethyleneimine (LPEI), branched polyethyleneimine (BPEI), polydopamine, poly(vinylamine), poly(allylamine), poly(l-lysine), aminated methylcellulose, and aminated ethylcellulose.

6. The separation membrane for olefin separation according to claim 1,
   wherein the sulfonated polymer is selected from the group consisting of sulfonated polysulfone, sulfonated polyetherether ketone, sulfonated polyimide, sulfonated polyamide, sulfonated polycarbonate, sulfonated cellulose acetate, sulfonated polyethylene, sulfonated polypropylene, sulfonated polyvinylidene fluoride, sulfonated polyvinyl chloride, sulfonated polyester, sulfonated polyacrylonitrile, sulfonated polystyrene, sulfonated butadiene, and copolymers thereof.

7. The separation membrane for olefin separation according to claim 1,
   wherein the transition metal is one or more metals selected from the group consisting of Ag, Cu, Ti, Hf, Zr, V, Nb, Ta, Mo, W, Tc, Re, Co, Rh, Ir, Ni, Pd, Pt, Zn, and Sn.

8. The separation membrane for olefin separation according to claim 1,
   wherein the electron acceptors are one or more selected from the group consisting of Tetrathiafulvalene, p-benzoquinone, and 7,7,8,8-tetracyanoquinodimethane (TCNQ).

9. The separation membrane for olefin separation according to claim 1,
   wherein the electron acceptors is contained in an amount of 1~15 parts by weight based on 100 parts by weight of the separation membrane composed of aminated polymer, sulfonated polymer or mixtures thereof; and transition metal.

10. The separation membrane for olefin separation according to claim 1,
    wherein the transition metal is crosslinked with aminated polymer, sulfonated polymer or mixtures thereof in an ionic state.

11. A composite membrane for olefin separation comprising:
    aminated polymer, sulfonated polymer or mixtures thereof;
    transition metal;
    electron acceptors; and
    porous support.

12. The composite membrane for olefin separation according to claim 11,
    wherein the porous support is selected from the group consisting of the porous supports, metal porous supports, and ceramic porous supports made of polysulfone, polyvinylidene fluoride, polyamide imide, polyether imide, or polyester.

* * * * *